US010330513B2

(12) United States Patent
Ricks et al.

(10) Patent No.: US 10,330,513 B2
(45) Date of Patent: Jun. 25, 2019

(54) MULTI-DYNAMIC-RANGE SENSOR (75) Inventors: Lamar Floyd Ricks, Lewis Center, OH (US); Ian Bentley, New Ipswich, NH (US); Paul Prehn Bey, Hilliard, OH (US)

(73) Assignee: Honeywell International Inc., Morris Plains, NJ (US)

( * ) Notice: Subject to any disclaimer, the term of this patent is extended or adjusted under 35 U.S.C. 154(b) by 1584 days.

(21) Appl. No.: 12/473,174

(22) Filed: May 27, 2009

(65) Prior Publication Data

US 2010/0305465 A1    Dec. 2, 2010

(51) Int. Cl.
*G01F 7/00* (2006.01)
*A61B 5/087* (2006.01)
*G01F 1/696* (2006.01)

(52) U.S. Cl.
CPC .............. *G01F 7/00* (2013.01); *A61B 5/0878* (2013.01); *G01F 1/696* (2013.01)

(58) Field of Classification Search
CPC .......... G01F 7/00; G01F 1/696; A61B 5/0878
USPC ............ 341/156, 113, 55; 600/538–540, 529
See application file for complete search history.

(56) References Cited

U.S. PATENT DOCUMENTS

| 3,484,732 A | 12/1969 | Postma |
| 3,726,271 A * | 4/1973 | Mondshine .......... A61B 5/0806 330/85 |
| 3,797,479 A * | 3/1974 | Graham ........................ 600/538 |
| 4,478,076 A | 10/1984 | Bohrer |
| 4,478,077 A | 10/1984 | Bohrer et al. |
| 4,501,144 A | 2/1985 | Higashi et al. |
| 4,574,640 A | 3/1986 | Krechmery |
| 4,581,928 A | 4/1986 | Johnson |
| 4,651,564 A | 3/1987 | Johnson et al. |
| 4,683,159 A | 7/1987 | Bohrer et al. |
| 4,733,559 A | 3/1988 | Aine et al. |

(Continued)

FOREIGN PATENT DOCUMENTS

| AU | 2010202036 A1 | 12/2010 |
| AU | 2010202036 B2 | 11/2015 |

(Continued)

OTHER PUBLICATIONS

"BDS Series Pressure Sensor," 4 pages, prior to Sep. 6, 2011.

(Continued)

*Primary Examiner* — Navin Nanithithadha
*Assistant Examiner* — Tho Q Tran
(74) *Attorney, Agent, or Firm* — Wick Phillips Gould & Martin, LLP (57) ABSTRACT

A sensing system that produces a multi-dynamic range output is provided. In an illustrative embodiment, a first channel and a second channel receive an analog output signal from a sensing element. The first channel provides a first digital output signal that has a first dynamic range, and the second channel provides a second digital output signal that has a second narrower dynamic range. In some cases, the second narrower dynamic range falls within the first dynamic range, and the first digital output signal may provide a first resolution and the second digital output signal may provide a second greater resolution. The dynamic range and/or resolution of one or more of the first channel and second channel may be dynamically reconfigurable, if desired.

20 Claims, 6 Drawing Sheets

(56) References Cited

U.S. PATENT DOCUMENTS

| | | | | |
|---|---|---|---|---|
| 4,845,649 | A | 7/1989 | Eckardt et al. | |
| 4,986,127 | A | 1/1991 | Shimada et al. | |
| 5,042,307 | A | 8/1991 | Kato | |
| 5,050,429 | A | 9/1991 | Nishimoto et al. | |
| 5,081,866 | A * | 1/1992 | Ochiai | A61B 5/0878 600/537 |
| 5,089,979 | A | 2/1992 | McEachern et al. | |
| 5,099,695 | A | 3/1992 | Sugano et al. | |
| 5,137,026 | A * | 8/1992 | Waterson | A61B 5/087 600/538 |
| 5,187,985 | A | 2/1993 | Nelson | |
| 5,193,393 | A | 3/1993 | Czarnocki | |
| 5,321,638 | A | 6/1994 | Witney | |
| 5,377,128 | A | 12/1994 | McBean | |
| 5,460,050 | A | 10/1995 | Miyano | |
| 5,507,171 | A | 4/1996 | Mattes et al. | |
| 5,518,002 | A * | 5/1996 | Wolf et al. | 600/538 |
| 5,544,529 | A | 8/1996 | Mitani et al. | |
| 5,562,101 | A * | 10/1996 | Hankinson et al. | 600/538 |
| 5,578,962 | A | 11/1996 | Rastegar | |
| 6,023,978 | A | 2/2000 | Dauenhauer et al. | |
| 6,035,240 | A * | 3/2000 | Moorehead et al. | 700/2 |
| 6,035,721 | A | 3/2000 | Krisch | |
| 6,047,244 | A | 4/2000 | Rud, Jr. | |
| 6,169,965 | B1 | 1/2001 | Kubisiak et al. | |
| 6,223,593 | B1 | 5/2001 | Kubisiak et al. | |
| 6,234,016 | B1 | 5/2001 | Bonne et al. | |
| 6,450,005 | B1 | 9/2002 | Bentley | |
| 6,502,459 | B1 | 1/2003 | Bonne et al. | |
| 6,542,594 | B1 | 4/2003 | LeBoulzec | |
| 6,653,959 | B1 | 11/2003 | Song | |
| 6,684,711 | B2 | 2/2004 | Wang | |
| 6,724,202 | B2 | 4/2004 | Tanizawa | |
| 6,894,632 | B1 * | 5/2005 | Robinson | H03M 1/005 341/143 |
| 7,085,628 | B2 | 8/2006 | Ohmi et al. | |
| 7,117,747 | B2 | 10/2006 | Borzabadi et al. | |
| 7,146,860 | B2 | 12/2006 | Yeh et al. | |
| 7,146,864 | B2 | 12/2006 | Sullivan et al. | |
| 7,185,538 | B2 | 3/2007 | Hager et al. | |
| 7,239,957 | B1 | 7/2007 | Sweet et al. | |
| 7,258,016 | B2 | 8/2007 | Maitland, Jr. et al. | |
| 7,262,724 | B2 * | 8/2007 | Hughes et al. | 341/139 |
| 7,265,346 | B2 * | 9/2007 | Whitehouse et al. | 250/287 |
| 7,266,999 | B2 | 9/2007 | Ricks | |
| 7,318,351 | B2 | 1/2008 | Cobianu et al. | |
| 7,343,812 | B2 | 3/2008 | Stewart et al. | |
| 7,377,177 | B1 | 5/2008 | Lamb et al. | |
| 7,469,598 | B2 | 12/2008 | Shkarlet et al. | |
| 7,520,051 | B2 | 4/2009 | Becke et al. | |
| 7,653,494 | B2 | 1/2010 | Neacsu et al. | |
| 7,759,945 | B2 | 7/2010 | Wade | |
| 7,769,557 | B2 | 8/2010 | Bey et al. | |
| 7,950,286 | B2 | 5/2011 | Bentley | |
| 8,010,322 | B2 | 8/2011 | Dmytriw et al. | |
| 8,024,146 | B2 | 9/2011 | Bey et al. | |
| 2002/0029003 | A1 * | 3/2002 | Mace | A61B 5/083 600/532 |
| 2004/0030766 | A1 * | 2/2004 | Witkowski | H04L 41/082 709/223 |
| 2007/0000330 | A1 | 1/2007 | Tysoe et al. | |
| 2007/0069000 | A1 | 3/2007 | Schubert | |
| 2007/0197922 | A1 | 8/2007 | Bradley et al. | |
| 2007/0271070 | A1 | 11/2007 | Dmytriw et al. | |
| 2008/0055130 | A1 * | 3/2008 | Sayers | H03M 1/188 341/139 |
| 2008/0107151 | A1 | 5/2008 | Khadkikar et al. | |
| 2008/0196507 | A1 | 8/2008 | Lamb et al. | |
| 2009/0073274 | A1 | 3/2009 | Dai | |
| 2010/0204602 | A1 * | 8/2010 | Addington et al. | 600/538 |
| 2010/0268485 | A1 | 10/2010 | Bey et al. | |
| 2011/0179879 | A1 | 7/2011 | Bentley | |

FOREIGN PATENT DOCUMENTS

| | | |
|---|---|---|
| CN | 1611932 A | 5/2005 |
| CN | 101040443 A | 9/2007 |
| CN | 101278838 A | 10/2008 |
| CN | 101897588 A | 12/2010 |
| CN | 101897588 B | 10/2014 |
| EP | 1477779 A1 | 11/2004 |
| EP | 1437577 B1 | 6/2006 |
| EP | 2256466 A2 | 12/2010 |
| JP | 2004077753 A | 3/2004 |

OTHER PUBLICATIONS

Celerity, Inc., "Dual Range Transducer Display," 2 pages, 2006.
Honeywell, "DCXL-DS Series, Sursense Ultra Low Silicon Pressure Sensors," 4 pages, May 2010.
Martel Electronics, "PPC-3300 Precision Dual Range Pressure Calibrator," 2 pages, 2002.
International Search Report for Corresponding Application No. EP10162964 dated Dec. 17, 2013.
Europe Patent Application No. 10162964.0, Communication pursuant to Article 94(3) EPC, dated Feb. 20, 2014, 3 pages.
Australia Patent Application No. 2010202036, Examination Report, dated Apr. 15, 2015, 3 pages.
Australia Patent Application No. 2010202036, Notice of Acceptance, dated Nov. 11, 2015, 2 pages.
China Patent Application 201010224027.0, Search Report, dated Sep. 2, 2013, 2 pages.
China Patent Application 201010224027.0, First Office Action, dated Sep. 12, 2013, 23 pages.
China Patent Application 201010224027.0, Second Office Action, dated Mar. 11, 2014, 8 pages.
China Patent Application 201010224027.0, Notification to Grant Patent Right, dated Jun. 27, 2014, 3 pages.

* cited by examiner

MULTI-DYNAMIC-RANGE SENSOR

FIELD

The present disclosure relates generally to sensors, and more particularly, to devices and methods for processing sensor data.

BACKGROUND

Sensors are commonly used to sense properties and/or parameters of a surrounding environment. A wide variety of sensors exists including sensors that are suitable for flow sensing, temperature sensing, pressure sensing, optical sensing, magnetic sensing, chemical sensing, force sensing, as well as others. Such sensors are used in a wide variety of applications across a wide variety of industries. For example, and in one particular example, flow sensors are used to sense the flow rate of a fluid (gas or liquid) in a fluid stream. Such flow sensors are commonly used in a wide variety of devices such as flow meters, respirometers, velocimeters, and in a wide variety of applications including, for example, flight control applications, industrial process stream applications, combustion control applications, weather monitoring applications, as well as many others. Other sensors are often used in a similar diverse range of applications.

Sensors often produce an analog output signal that represents a sensed property and/or parameter, across a relatively wide dynamic range of the sensed property and/or parameter. Continuing with the flow sensor example, a flow sensor may sense a flow rate in a fluid stream across a dynamic range of, for example, zero to 300 liters per minute. The output signal of such a flow sensor may be provided to an Analog-to-Digital Converter (ADC), which converts the analog output signal of the sensor into a digital signal that can be read and understood by a microprocessor or the like. The number of bits of the particular Analog-to-Digital Converter (ADC) used typically defines the resolution across the dynamic range of the sensor.

SUMMARY

The present disclosure relates generally to sensors, and more particularly, to devices and methods for processing sensor data. In one illustrative example, a sensing element is provided that is configured to produce an analog output signal that represents a sensed property and/or parameter. A first channel is provided for receiving the analog output signal from the sensing element. The first channel includes a first Analog-to-Digital Converter (ADC) and provides a first digital output signal that has a wider dynamic range. A second channel is also provided for receiving the analog output signal from the sensing element. The second channel includes a second Analog-to-Digital Converter (ADC) and provides a second digital output signal that has a narrower dynamic range than the first channel. In some cases, the narrower dynamic range is a subset of the wider dynamic range, but this is not required. Also, and in some cases, the resolution of the first channel across the wider dynamic range is less than the resolution of the second channel across the narrower dynamic range, but again, this is not required.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION

The disclosure may be more completely understood in consideration of the following detailed description of various illustrative embodiments of the disclosure in connection with the accompanying drawings, in which.

DESCRIPTION

The following description should be read with reference to the drawings wherein like reference numerals indicate like elements throughout the several views. The detailed description and drawings show several embodiments which are meant to be illustrative of the claimed invention. While the description below uses a flow sensor as an example, it should be recognized that the present invention may be equally applied to other sensors or sensor applications including, for example, flow sensing, temperature sensing, pressure sensing, optical sensing, magnetic sensing, chemical sensing, force sensing, as well as others, as desired.

Figure 1:
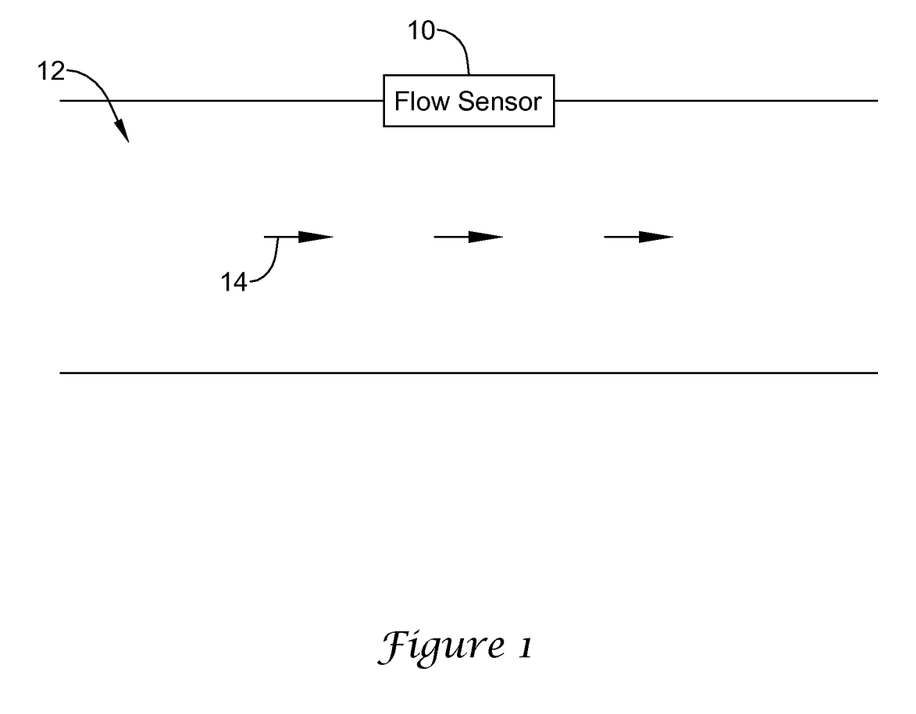
FIG. 1 is a schematic diagram of an illustrative flow sensor for measuring a fluid flow rate of a fluid in a fluid stream.

FIG. 1 is a schematic diagram of an illustrative flow sensor 10 for measuring a fluid flow rate of a fluid 14 in a fluid stream 12. The term "fluid" as used herein can refer to a gas flow or a liquid flow, depending on the application. In the illustrative embodiment, the flow sensor 10 may be disposed in or adjacent to the fluid stream 12 to measure one or more properties of the fluid flow 14. For example, the flow sensor 10 may measure the mass flow and/or velocity of the fluid flow 14 using one or more thermal sensors (e.g. see FIG. 2), pressure sensors, acoustical sensors, optical sensors, pitot tubes, and/or any other suitable sensor or sensor combination, as desired. In some cases, the flow sensor 10 may be a microbridge or a Microbrick™ sensor assembly available from the assignee of the present application, but this is not required. Some illustrative methods and sensor configurations that are suitable for measuring the mass flow and/or velocity of the fluid flow 14 are disclosed in, for example, U.S. Pat. Nos. 4,478,076; 4,478,077; 4,501, 144; 4,581,928; 4,651,564; 4,683,159; 5,050,429; 6,169, 965; 6,223,593; 6,234,016; and 6,502,459. It must be recognized, however, that flow sensor 10 may be any suitable flow sensor, as desired.

In the illustrative example, the fluid stream 12 may have a range of flow rates of fluid flow 14. For example, the fluid stream 12 may include a high-volume fluid flow, a mid-volume fluid flow, or a low-volume fluid flow. An example low-volume fluid flow application may be a respirometer for measuring the respiration of a person, such as an infant.

Other example fluid flow applications can include, but are not limited to, respirometers for an adult, flow meters, velocimeters, flight control, industrial process stream, combustion control, weather monitoring, as well as any other suitable fluid flow applications, as desired.

Figure 2:
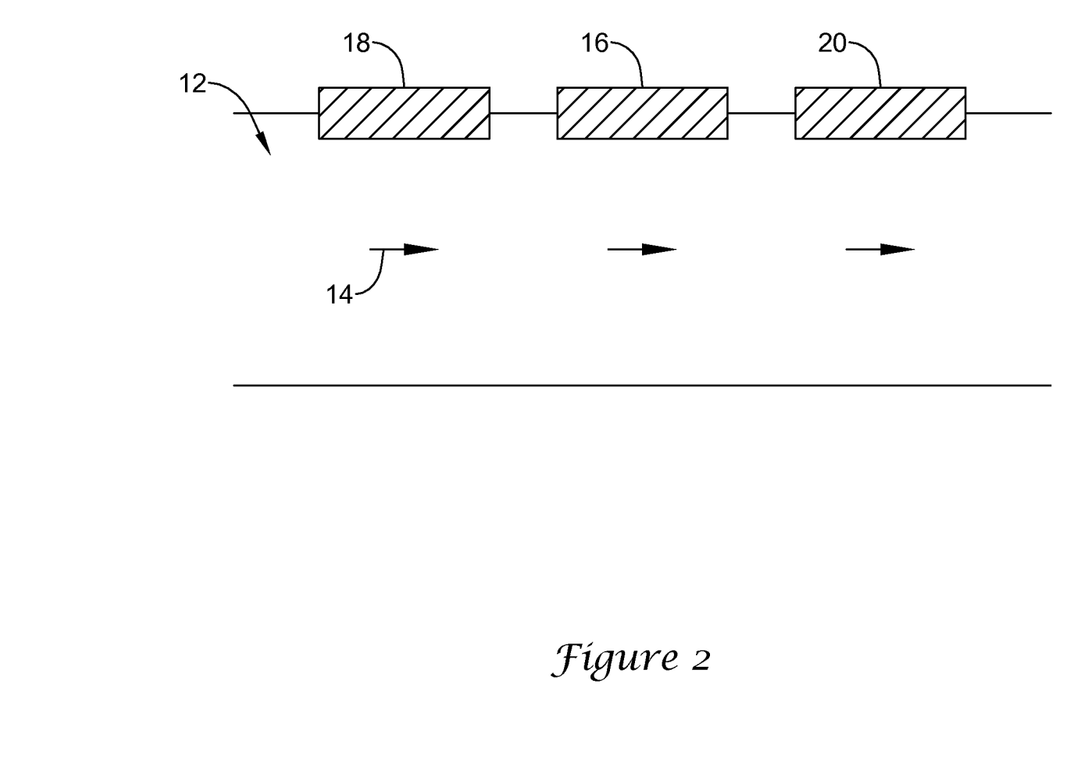
FIG. 2 is a schematic diagram of an illustrative thermal flow sensor assembly for measuring the flow rate of a fluid in a fluid stream.

Turning now to FIG. 2, which is a schematic diagram of an illustrative embodiment of a thermal flow sensor assembly for measuring the flow rate of a fluid flow 14 in a fluid stream 12. In the illustrative embodiment, the flow sensor assembly may include one or more heater elements, such as heater element 16, and one or more sensor elements 18 and 20. As illustrated, the sensor assembly includes a heater element 16, a first sensor element 18 positioned upstream of the heater element 16, and a second sensor element 20 positioned downstream of the heater element 16. In the example shown, when no fluid flow is present in the fluid stream 12 and the heater element 16 is heated to a temperature higher than the ambient temperature of the fluid in the fluid flow 14, a temperature distribution may be created and transmitted in a generally symmetrical distribution about the heater element 16 to upstream sensor element 18 and downstream sensor element 20. In this example, upstream sensor element 18 and downstream sensor element 20 may sense the same or similar temperature (e.g. within 25 percent, 10 percent, 5 percent, 1 percent, 0.001 percent, etc.). When a fluid flow 14 is present in the fluid stream 12 and the heater element 16 is heated to a temperature higher than the ambient temperature of the fluid in the fluid flow 14, the symmetrical temperature distribution may be disturbed and the amount of disturbance may be related to the flow rate of the fluid flow 14 in the fluid stream 12. The flow rate of the fluid flow 14 may cause the upstream sensor element 18 to sense a relatively cooler temperature than the downstream sensor element 20. In other words, the flow rate of the fluid flow 14 may cause a temperature differential between the upstream sensor element 18 and the downstream sensor element 20 that is related to the flow rate of the fluid flow in the fluid stream 12.

In another illustrative embodiment, the mass flow and/or velocity of the fluid flow 14 may be determined by providing a transient elevated temperature condition in the heater element 16, which in turn, causes a transient elevated temperature condition (e.g. heat pulse) in the fluid flow 14. When there is a non-zero flow rate in the fluid flow 14, the upstream sensor element 18 may receive a transient response later than the downstream sensor element 20. The flow rate of the fluid flow 14 can then be computed using the time lag between the upstream sensor element 18 and downstream sensor element 20, or between the time the heater is energized and when the corresponding elevated temperature condition (e.g. heat pulse) is sensed by one of the sensors, such as the downstream sensor 20.

Further, it is to be understood that the illustrative heater element 16 is optional and, in some embodiments, may not be present, as desired. For example, one or more pressure sensors, acoustical sensors, optical sensors, pitot tubes, and/or any other suitable sensor or sensor combination may be used, as desired.

Figure 3:
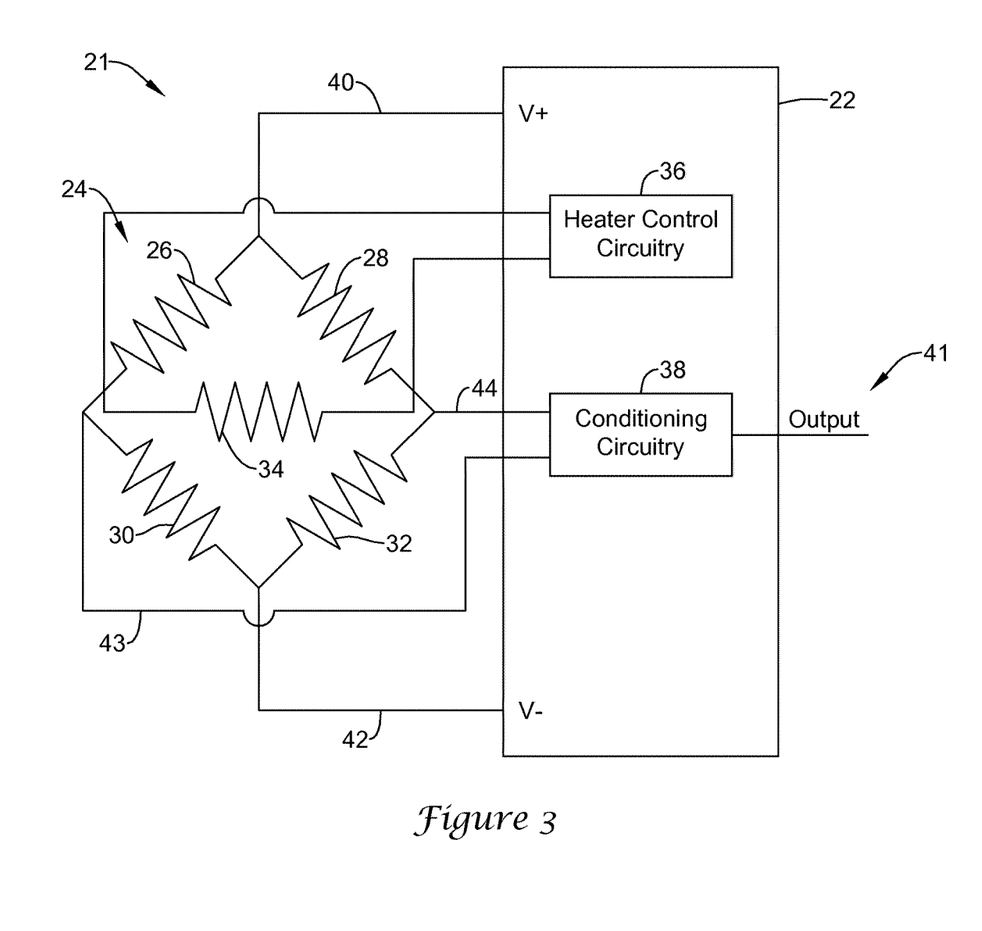
FIG. 3 is a schematic diagram of an illustrative flow sensor assembly.

FIG. 3 is a schematic diagram of an illustrative flow sensor assembly 21. In the illustrative embodiment, the sensor assembly 21 includes a sensing element 24 and flow sensing processing circuitry 22. As shown, the sensing element 24 may include a heater resistor 34 and a number of sensor resistors 26, 28, 30, and/or 32. In the illustrative embodiment, the resistors 26, 28, 30, and 32 are arranged in a Wheatstone bridge configuration, but this is not required in all embodiments.

At least one of the resistors 26, 28, 30, and 32 may be thermally sensitive resistors that have a relatively large positive or negative temperature coefficient, such that the resistance varies with temperature. In one example, resistors 30 and 32 may be thermally sensitive resistors. In another example, all of resistors 26, 28, 30 and 32 may be thermally sensitive resistors. In some cases, the thermally sensitive resistors 26, 28, 30, and/or 32 may be thermistors. However, it is contemplated that any suitable thermally sensitive resistor may be used, as desired.

The thermally sensitive resistors 26, 28, 30, and/or 32 may be arranged so that one or more of the resistors 26, 28, 30, and 32 are positioned upstream of the heater resistor 34, and one or more of the resistors 26, 28, 30, and 32 are positioned downstream of heater resistor 34, similar to that shown in FIG. 2. In one example, resistors 26 and 32 may be positioned upstream of heater resistor 34, and resistors 28 and 30 may be positioned downstream of heater resistor 34. In another example, resistor 26 may be positioned upstream of heater resistor 34, and resistor 28 may be positioned downstream of heater resistor 34, with resistors 30 and 32 being non-thermally sensitive resistors positioned away from the flow stream. It is contemplated, however, that other configurations may be used.

As illustrated, a positive supply voltage may be provided at node 40, which is coupled to a first terminal of resistor 26 and a first terminal of resistor 28, as shown. The positive supply voltage at node 40 may be provided by sensing circuitry 22, as shown. A negative supply voltage may be provided at node 42, which is coupled to a second terminal of resistor 30 and a second terminal of resistor 32, as shown. The negative supply voltage at node 42 may be provided by flow sensing circuitry 22. A second terminal of resistor 26 may be coupled to a first terminal of resistor 30 at node 43, and a second terminal of resistor 28 may be coupled to a first terminal of resistor 32 at node 44 to form the Wheatstone bridge. Nodes 43 and 44 may form an output of the Wheatstone bridge In the illustrative embodiment, the sensor assembly 21 may be calibrated such that little or no voltage will be produced between nodes 43 and 44 when zero flow exists in a fluid stream of interest. As discussed above, when no flow exists, both the upstream and downstream thermally sensitive resistors will be heated by the heater element 34 to the same degree, and thus the Wheatstone bridge will be in balance. However, when a non-zero flow rate exists in the fluid stream of interest, an analog voltage will be produced at the output nodes 43 and 44 of the Wheatstone bridge. As discussed above, this analog voltage will be related to the flow rate of the fluid stream of interest.

In the illustrative embodiment of FIG. 3, flow sensing circuitry 22 is provided. Flow sensing circuitry 22 may be implemented in an integrated circuit, such as an application specific integrated circuit (ASIC), if desired. However, this is not required. For example, flow sensing circuitry 22 may be implemented as separate electrical components secured to a printed circuit board, and/or may be implemented as some combination of hardware and software, as desired.

As illustrated, the flow sensing circuitry 22 may include heater control circuitry 36 and conditioning circuitry 38. The heater control circuitry 36 may be configured to selectively activate and/or deactivate the heater resistor 34 by, for example, providing a current flow through the heater resistor 34. As the current passes through heater resistor 34, the heater resistor 34 may heat up causing a temperature distribution in the fluid stream. In some cases, the heater control circuit 36 may provide a current pulse through the heater resistor 34 to cause a heat pulse in the fluid stream.

Conditioning circuitry 38 may be electrically coupled to output nodes 43 and 44 of the Wheatstone bridge. The conditioning circuitry 38 may include, for example, amplification, digitization, linearization, temperature compensation, calibration, translation, as well as other functions, as desired. The conditioning circuitry 38 may input the analog output signal that is present between nodes 43 and 44 of the Wheatstone bridge and provide at least one digital output signal 41. As illustrated, the conditioning circuitry 38 may provide a single output 41, however, it is contemplated that multiple outputs, each of which have a different dynamic range and/or resolution, may be provided. In some cases, it is contemplated that the output 41 of conditioning circuitry 38 may be or include an analog output signal, if desired.

Figure 4:
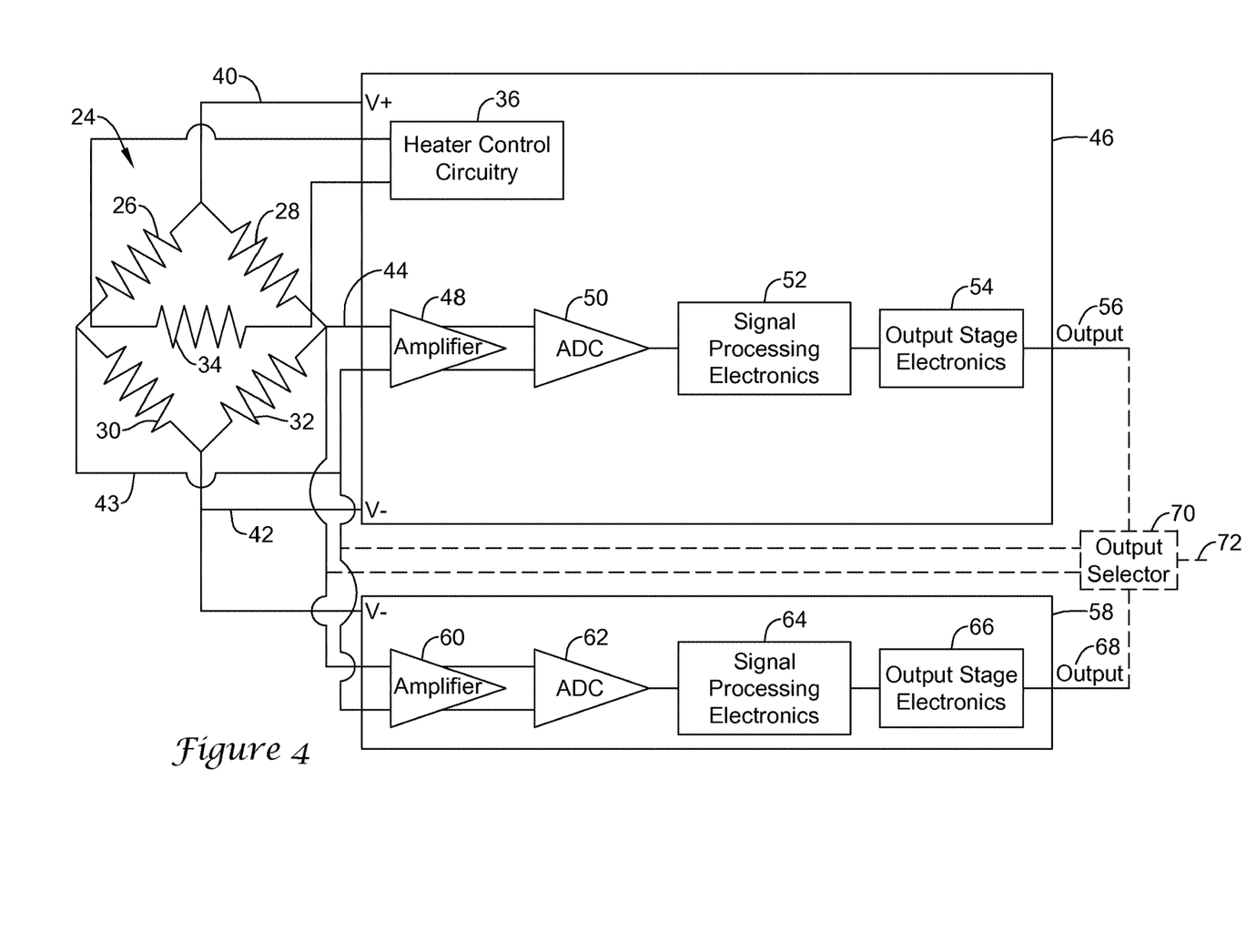
FIG. 4 is a schematic diagram of an illustrative flow sensor assembly having multiple channels.

Turning now to FIG. 4, which shows a schematic diagram of an illustrative flow sensor assembly having multiple channels. In the illustrative embodiment of FIG. 4, the sensor element 24 includes a heater resistor 34 and a number of thermally sensitive resistors 26, 28, 30, and 32, similar to that shown and described above with respect to FIG. 3. However, it is contemplated that the sensor element 24 may be any suitable sensor including, for example, any suitable flow sensor, temperature sensor, pressure sensor, optical sensor, magnetic sensor, chemical sensor, force sensor, or any other suitable sensor as desired.

In the illustrative embodiment of FIG. 4, output nodes 43 and 44 of sensor element 24 are shown electrically connected to a number of integrated circuits, such as integrated circuit 46 and integrated circuit 58, via a number of channels or signal paths. For example, sensor element 24 outputs 43 and 44 may each have a first signal path or channel coupled to integrated circuit 46, and a second signal path or channel coupled to integrated circuit 58. While only two integrated circuits 46 and 58 are shown in FIG. 4, it is contemplated that any number of integrated circuits may be used, as desired. Also, while integrated circuits 46 and 58 are shown, it is contemplated that these may be implemented using separate electrical components secured to a printed circuit board, and/or may be implemented as some combination of hardware and software, as desired.

Each integrated circuit 46 and 58 may be part of a separate signal path or channel. In the illustrative embodiment, integrated circuit 46 includes an amplifier 48, an analog-to-digital converter (ADC) 50, signal processing electronics 52, and output stage electronics 54. Likewise, integrated circuit 58 includes an amplifier 60, an analog-to-digital converter (ADC) 62, signal processing electronics 64, and output stage electronics 66. In some embodiments, integrated circuits 46 and 58 may have the same design and/or circuitry, which, in some cases, may provide greater output granularity, but this is not required. The amplifiers 48 and 60 may be configured to amplify the analog signal between outputs 43 and 44 of the Wheatstone bridge of sensing element 24. The amplifiers 48 and 60 may be configured to have the same or different gain.

In some cases, the amplifiers 48 and 60 may be configured and calibrated to amplify the corresponding analog signal at the outputs 43 and 44 of the Wheatstone bridge according to a desired dynamic range for the respective signal path or channel. For example, amplifier 60 may be configured to have a larger gain than amplifier 48 if the signal path or channel of integrated circuit 58 is configured to have a narrower dynamic range than the dynamic range of the signal path or channel of integrated circuit 46.

The Analog-to-Digital Converters (ADC) 50 and 62 may receive the amplified analog signals from the corresponding amplifiers 48 and 60, and convert the corresponding amplified analog signal into a digital signal for further processing. The Analog-to-Digital Converters (ADC) 50 and 62 may include a number of bits, for example, Analog-to-Digital Converters (ADC) 50 and 62 may each be 6 bits, 7 bits, 8 bits, 9 bits, 10 bits, 11 bits, 12 bits, 13 bits, 14 bits, 15 bits, 16 bits, or any other number of bits, as desired. In some cases, Analog-to-Digital Converters (ADC) 50 may have a common number of bits as Analog-to-Digital Converters (ADC) 62, but this is not required. The number of quantization levels of the Analog-to-Digital Converters (ADC) has a power of two such that, for example, a 8 bit Analog-to-Digital Converter (ADC) may encode an analog input signal to 256 quantization levels (i.e. $2^8=256$), and a 14 bit Analog-to-Digital Converter (ADC) may encode an analog input signal to 16,384 quantization levels.

The resolution of a channel may be defined generally by dividing the dynamic range of the channel by the number of quantization levels of the corresponding Analog-to-Digital Converter (ADC). For example, in a respirometers application, if the dynamic range of the first channel or signal path of the integrated circuit 46 is 0 to 300 liters per minute, and the Analog-to-Digital Converter (ADC) 50 has 14 bits, the resolution would be about 0.018 liters per minute. Similarly, if the dynamic range of the second channel or signal path of the integrated circuit 58 is 0 to 30 liters per minute, and the Analog-to-Digital Converter (ADC) 62 has 14 bits, the resolution would be 0.0018 liters per minute, or about 10 times the resolution of the wider dynamic range of the first channel or signal path 46 in the preceding examples. In some embodiments, the dynamic range of Analog-to-Digital Converter (ADC) 62 and/or Analog-to-Digital Converter (ADC) 50 may be dynamically configurable and/or reconfigurable. As such, the dynamic range of the first and/or second signal paths or channels may be increased, decreased, or shifted, as desired. The gain of the amplifiers 48 and 60 may be likewise configurable and/or reconfigurable.

In some embodiments, the dynamic range of the first channel or signal path of the integrated circuit 46 and/or the dynamic range of the second channel or signal path of the integrated circuit 58 may be dynamically configurable and/or reconfigurable with software, electronic adjustments, additional discrete circuitry, and/or any other suitable manner. In some software controlled cases, commands may be sent to the integrated circuits 46 and/or 58 or portions thereof from, for example, an internal or external controller to dynamically reconfigure the first channel and/or second channel. In one example, amplifiers 48 and/or 60 may have a gain and an offset adjustable by the internal or external controller to cause a level shift and/or gain shift in the first channel and/or second channel. However, any other way of increasing, decreasing, and/or shifting the dynamic range of the first and/or second signal paths or channels may be used, as desired.

In some cases, the dynamic range of the first channel or signal path and the dynamic range of the second channel or signal path may fully overlap, partially overlap, or not-overlap, as desired. In one example, the dynamic range of the second channel or signal path of the integrated circuit 58 may be a subset of the dynamic range of the first channel or signal path of the integrated circuit 46, if desired. When so provided, the digital output signal from Analog-to-Digital Converter (ADC) 50 may have a first resolution, and the digital output signal from Analog-to-Digital Converter (ADC) 62 may have a second resolution that is greater than the first resolution, but across a narrower dynamic range (assuming equal quantization levels in Analog-to-Digital Converters (ADC) 50 and 62).

The digital output signal of Analog-to-Digital Converter (ADC) 50 and Analog-to-Digital Converter (ADC) 62 may be input into corresponding signal processing electronics 52 and 64 for further processing. In some cases, signal processing electronics 52 and 64 may be configured to perform linearization, temperature compensation, calibration, translation, and/or other signal processing on the digital output signals, as desired. The processed digital signal may then be input into a corresponding output stage electronics block 54 and 66. The output stage electronics blocks 54 and 66 may process the digital signal according to a desired output (analog or digital). In some cases, each integrated circuit 46 and 58 may have an output 56 and 68 to provide a corresponding digital output signal.

In some embodiments, an optional output selector 70 may be provided to provide a single output 72 for the sensor. In one example, an optional output selector may have a first input coupled output 56 of the first channel, and a second input coupled to output 68 of the second channel. The output selector 70 may be configured to output either output signal 56 or output signal 68 on output 72 according to a control signal. In one example, the control signal of the output selector 70 may include connections to the analog output signals 43 and 44 of the Wheatstone bridge of the sensor element 24. In this example, the output selector 70 may select digital output signal 68 if the analog output signal 43 and 44 is within the dynamic range of the second channel, and may select the digital output signal 56 if the analog output signal 43 and 44 is outside of the dynamic range of the second channel. This is just one example. Further, it is contemplated that the output selector 70 may be manually or electronically adjusted by a user or controller to select a desired output, as desired. In other cases, it is contemplated that the output selector 70 may multiplex the digital output signals 56 and 68 into a single output signal on output 72, if desired. In one example respiration application, the first channel may be configured to sense fluid flow of an infant and the second channel may be configured to sense fluid flow of an adult. In this application, the output selector 70 may be configured to automatically select output 56 of the first channel or output 68 of the second channel according to the dynamic range of analog outputs 43 and 44.

In the illustrative embodiment, the optional output selector 70 is shown separate from integrated circuits 56 and 68. However, it is contemplated that optional output selector 70 may be incorporated into integrated circuit 56 and/or integrated circuit 68, as desired. Further, the heater control circuitry 36 is shown as implemented by integrated circuit 56. However, it is contemplated that heater control circuitry 36 may be included in integrated circuit 68, or provided separately, if desired.

Figure 5:
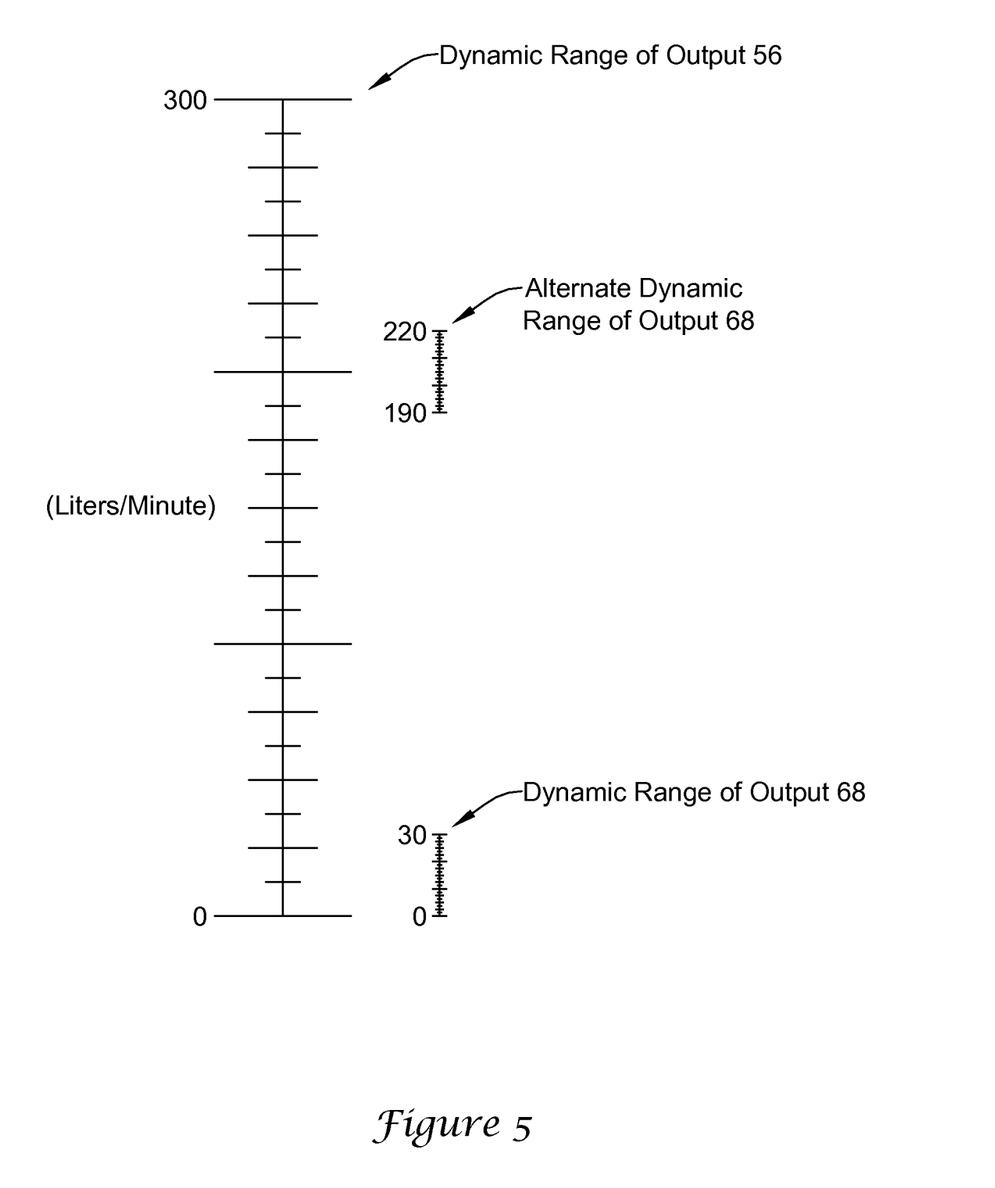
FIG. 5 is a graphical diagram showing illustrative dynamic ranges for the channels the flow sensor assembly of FIG. 4.

FIG. 5 is a graphical diagram showing illustrative dynamic ranges for the first and second channels the flow sensor assembly of FIG. 4. Taking the respirometer application as an example, the dynamic range of digital output signal 56 may be, for example, 0 to 300 liters per minute and the dynamic range of digital output signal 68 may have a narrower dynamic range, such as for example, 0 to 30 liters per minute. These, however, are only illustrative.

Assuming that the Analog-to-Digital Converters (ADC) 50 and 62 of FIG. 4 have the same number of bits, the resolution of the narrower dynamic range output signal 68 would be greater than the resolution of the wider dynamic range output 56, as indicated by the closer spaced horizontal lines in FIG. 5. Also, and as shown, the dynamic range of digital output signal 68 is a subset of the dynamic range of output signal 56, but this is not required. It is contemplated that the dynamic range of digital output signal 68 may overlap, partially overlap or not overlap with the dynamic range of output signal 56, as desired.

As indicated above, it is contemplated that the dynamic range of the digital output signal 68 and/or digital output signal 56 may be configurable and/or reconfigurable. For example, as shown, the dynamic range of digital output signal 68 is from 0 to 30 liters per minute. However, it is contemplated that the dynamic range of digital output signal 68 may be reconfigured to be 10 to 40 liters per minute, 290 to 300 liters per minute. For example, an alternative dynamic range from 190 to 220 liters per minute of digital output signal 68 is shown. Also, it is contemplated that the dynamic range may be increased or decreased, as desired. For example, the dynamic range may be reconfigured to have a dynamic range of 10 to 30 liters per minute, or 100 to 200 liters per minute. The resolution may be likewise reconfigurable. In some cases, the dynamic range, resolution and/or other parameters may be dynamically reconfigured on the fly with, for example, software, a feedback line, and/or any other suitable method or circuitry, as desired. In one example, the first channel and/or the second channel may dynamically track the range of analog outputs 43 and 44. However, any other suitable method of dynamically reconfiguring the dynamic range, resolution, and/or other parameters may be use, as desired.

Although not shown, and as indicated above, it is contemplated that the dynamic range of digital output signal 56 and the dynamic range of digital output signal 68 may be non-overlapping. For example, the dynamic range of digital output signal 68 may be about 0 to 30 liters per minute, and the dynamic range of digital output signal 56 may be about 30 to 330 liters per minute. Further, it is contemplated that the dynamic ranges of each channel may be configured to have the same resolution such as, for example, the dynamic range of digital output signal 56 may be 0 to 150 liters per minute and the dynamic range of digital output signal 68 may be 151 to 300 liters per minute, if desired. Further, it is to be understood that the foregoing dynamic ranges, resolutions, and number of bits of the Analog-to-Digital Converters (ADC) 50 and 62 is merely illustrative and is not meant to be limiting in any manner. It is contemplated that any suitable dynamic ranges, resolutions, and number of bits of the Analog-to-Digital Converters (ADC) may be used, as desired.

Figure 6:
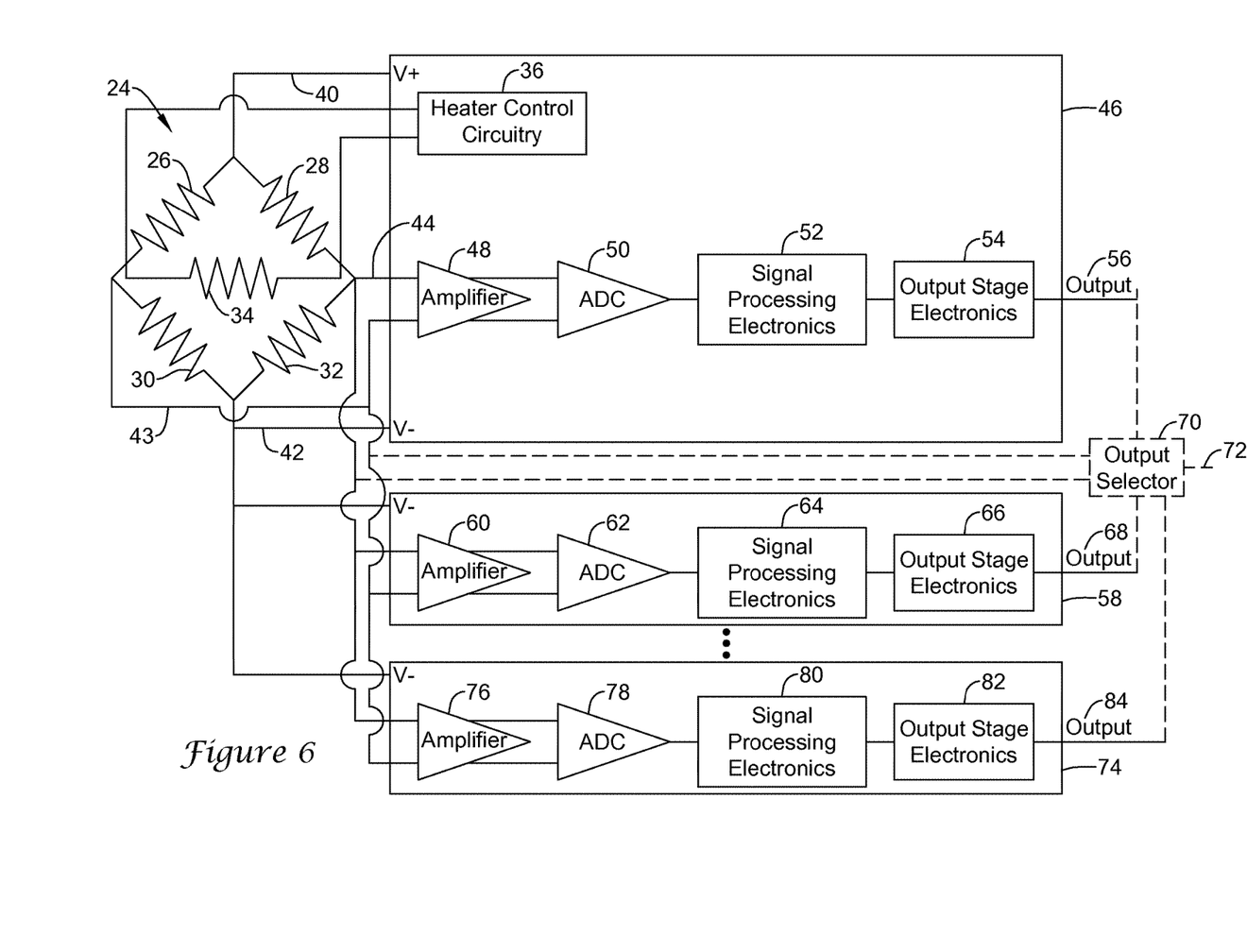
FIG. 6 is a schematic diagram of another illustrative flow sensor assembly having multiple channels.

Turning now to FIG. 6, which shows a schematic diagram of another illustrative flow sensor assembly having multiple channels. In the illustrative embodiment of FIG. 6, the sensor element 24 includes a heater resistor 34 and a number of thermally sensitive resistors 26, 28, 30, and 32, similar to that shown and described above with respect to FIGS. 3 and 4. However, it is contemplated that the sensor element 24 may be any suitable sensor including, for example, any suitable flow sensor, temperature sensor, pressure sensor, optical sensor, magnetic sensor, chemical sensor, force sensor, or any other suitable sensor as desired.

In the illustrative embodiment of FIG. 6, output nodes 43 and 44 of sensor element 24 are shown electrically connected to N integrated circuits, such as integrated circuit 46, integrated circuit 58, and integrated circuit 74. While only three integrated circuits 46, 58, and 74 are shown in FIG. 6, it is contemplated that any number of integrated circuits may be used, such as one, two, three, four, five six, seven, or more integrated circuits, as desired. In such an embodiment, sensor element 24 outputs 43 and 44 may each have N signal paths or channels, such as a first signal path or channel coupled to integrated circuit 46, a second signal path or channel coupled to integrated circuit 58, and a third signal path or channel coupled to integrated circuit 74. In the illustrative embodiment, integrated circuit 74 may include an amplifier 76, an analog-to-digital converter (ADC) 78, signal processing electronics 80, and output stage electronics 82 similar to integrated circuits 46 and 58 discussed above. Integrated circuit 74 may output a digital output signal 84 having a dynamic range and/or resolution, which, in some cases, may be input into the output selector similar to digital output signals 56 and 68.

Similar to embodiments discussed above, it is contemplated that the dynamic range of the digital output signal 84, as well as any additional output signal from the N channels or signal paths, may be configurable and/or reconfigurable, similar to the dynamic range of digital output signals 56 and 68 discussed above. Further, it is contemplated that the dynamic range of digital output signal 56, the dynamic range of digital output signal 68, the dynamic range of digital output 84, as well as the dynamic range of any other digital output signals of the N channels or signal paths not shown, may be overlapping, non-overlapping, or any combination of overlapping and non-overlapping outputs, as desired. Further, it is contemplated that the dynamic ranges of each channel or signal path may be configured to have the same resolution or different resolution, as desired.

Having thus described the preferred embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respects, only illustrative. Changes may be made in details, particularly in matters of shape, size, and arrangement of parts without exceeding the scope of the invention. The scope is, of course, defined in the language in which the appended claims are expressed.

What is claimed is:

1. A respiration sensing system for sensing respiration of a patient, the respiration sensing system comprising:
   a sensing element configured to sense a respiration flow rate, the sensing element configured to provide an analog output signal that is related to the sensed respiration flow rate;
   a first channel configured to receive the analog output signal from the sensing element, the first channel including a first amplifier having a first gain and a first offset for providing a first amplified output signal to a first Analog-to-Digital Converter (ADC), the first amplifier in combination with the first Analog-to-Digital Converter (ADC) providing a first digital output signal that has a first dynamic range and a first resolution, the first resolution corresponding to a quantization of the first dynamic range using a first quantization level of the first ADC, wherein the first amplified output signal is offset, wherein the first ADC is included within the respiration sensing system;
   a second channel configured to receive the analog output signal from the sensing element, the second channel including a second amplifier having a second gain different from the first gain for providing a second amplified output signal to a second Analog-to-Digital Converter (ADC), the second amplifier in combination with the second Analog-to-Digital Converter (ADC) providing a second digital output signal that has a second dynamic range and a second resolution, the second resolution corresponding to a quantization of the second dynamic range using a second quantization level of the second ADC, and wherein the second dynamic range is narrower than the first dynamic range, and the second resolution is higher than the first resolution, wherein the second amplified output signal is offset, wherein the second ADC is included within the respiration sensing system;
   an output selector, formed as an integrated circuit, configured to receive the analog output signal from the sensing element and output the first digital output signal or the second digital output signal according to the analog output signal received by the output selector, wherein the output selector is configured to select and output the second digital output signal if the analog output signal is within the dynamic range of the second ADC and to select and output the first digital output signal if the analog output signal is outside the dynamic range of the second ADC;
   wherein the output selector is configured to receive the first digital output signal for all analog output signals over the entire first dynamic range, and wherein the output selector is configured to receive the second digital output signal for all analog output signals over the entire second dynamic range; and
   wherein the first offset and the second offset are adjustable and are configured to cause a level shift and/or a gain shift in the first channel and/or the second channel.

2. The respiration sensing system of claim 1, wherein the second dynamic range is a subset of the first dynamic range.

3. The respiration sensing system of claim 1, wherein a number of bits of the quantization level of the first ADC is the same as a number of bits of the quantization level of the second ADC.

4. The respiration sensing system of claim 1, further comprising a third channel configured to receive the analog output signal from the sensing element, the third channel including a third Analog-to-Digital Converter (ADC) and providing a third digital output signal that has a third dynamic range different than the first and second dynamic ranges.

5. The respiration sensing system of claim 1, wherein the first dynamic range and/or the second dynamic range is dynamically reconfigurable.

6. The respiration sensing system of claim 1, further comprising signal processing electronics configured to perform linearization, temperature compensation, calibration, and/or translation on the first digital output signal and the second digital output signal; and wherein the first gain is equal to one.

7. A flow sensing system for sensing a fluid flow in a fluid stream, the flow sensing system comprising:
   a sensing element configured to sense a fluid flow in a fluid stream, the sensing element configured to provide an analog output signal that is related to the sensed fluid flow;
   a first channel configured to receive the analog output signal from the sensing element, the first channel including a first amplifier having a first offset, provided in the first amplifier, for providing a first amplified output signal to a first Analog-to-Digital Converter (ADC), the first amplifier in combination with the first Analog-to-Digital Converter (ADC) providing a first digital output signal that has a first dynamic range, wherein the first amplified output signal is offset, wherein the first ADC is included within the flow sensing system; and a second channel configured to receive the analog output signal from the sensing element, the second channel including a second amplifier having a second offset, provided in the second amplifier, different from the first offset for providing a second amplified output signal to a second Analog-to-Digital Converter (ADC), the second amplifier in combination with the second Analog-to-Digital Converter (ADC) configured to provide a second digital output signal that has a second dynamic range, wherein the second amplified output signal is offset, wherein the second ADC is included within the flow sensing system;

and an output selector, formed as an integrated circuit, configured to receive the analog output signal from the sensing element and select and output either the first digital output signal or the second digital output signal according to the analog output signal. received by the output selector, wherein:

the second dynamic range is narrower than the first dynamic range, the second dynamic range falls within or substantially falls within the first dynamic range, and a starting value of the first dynamic range is different than starting value of the second dynamic range as dictated by the first offset and the second offset;

wherein the first digital output signal has a first resolution corresponding to a quantization of the first dynamic range and the second digital output signal has a second resolution corresponding to a quantization of the second dynamic range, wherein the second resolution is greater than the first resolution;

wherein the first offset and the second offset are adjustable and are configured to cause a level shift and/or a gain shift in the first channel and/or the second channel; and wherein the output selector is configured to select and output one of the first digital output signal or the second digital output signal based on the analog output signal from the sensing element.

8. The flow sensing system of claim 7, further comprising a third channel configured to receive the analog output signal from the sensing element, the third channel including a third amplifier having a third offset for providing a third amplified output signal to a third ADC, the third amplifier and the third ADC configured to provide a third digital output signal that has a third dynamic range different than the first dynamic range and the second dynamic range.

9. The flow sensing system of claim 7, wherein the quantization levels of the first ADC and the second ADC correspond to a common number of bits.

10. The flow sensing system of claim 7, wherein the sensing element includes a heat source and a number of temperature sensors.

11. The flow sensing system of claim 10, wherein at least one of the temperature sensors is positioned upstream of the heat source and at least one of the temperature sensors is positioned downstream of the heat source.

12. The flow sensing system of claim 11, wherein the heat source and the number of temperature sensors are configured so that a flow rate of the fluid flow in a fluid stream creates a temperature differential between the at least one of the temperature sensors that is positioned upstream of the heat source and the at least one of the temperature sensors that is positioned downstream of the heat source.

13. The flow sensing system of claim 7, wherein the output selector is configured to provide the second digital output signal if the analog output signal is within the dynamic range of the second ADC and is configured to provide the first digital output signal if the analog output signal is outside the dynamic range of the second ADC.

14. The flow sensing system of claim 7, wherein the second dynamic range is dynamically reconfigurable.

15. The flow sensing system of claim 7, wherein the first amplifier has a first gain and the second amplifier has a second gain, wherein the second gain is higher than the first gain.

16. A method for sensing a fluid flow in a fluid stream, the method comprising:

sensing a fluid flow in a fluid stream with a sensing element and providing an analog signal that is related to the sensed fluid flow;

amplifying the sensed analog signal with a first amplifier having a first gain and a first offset to provide a first amplified analog signal;

offsetting the first amplified analog signal with the first amplifier;

converting the first amplified analog signal to a first digital signal with a first Analog- to-Digital Converter (ADC) having a first number of quantization levels to provide a first digital output signal that has a first dynamic range;

amplifying the sensed analog signal with a second amplifier having a second gain and a second offset to provide a second amplified analog signal, wherein the second gain is different than the first gain, wherein the first offset and the second offset are adjustable and are configured to cause a level shift and/or a gain shift in the first channel and/or the second channel;

offsetting the second amplified analog signal with the second amplifier;

converting the second amplified analog signal to a second digital signal with a second Analog-to-Digital Converter (ADC) having a second number of quantization levels to provide a second digital output signal that has a second dynamic range, wherein the second dynamic range is narrower than the first dynamic range, and the second dynamic range falls within or substantially falls within the first dynamic range;

providing the sensed analog signal, the first digital signal, and the second digital signal to an output selector formed as an integrated circuit;

selecting and outputting the second digital signal with an output selector according to the sensed analog signal provided to output selector if the sensed analog signal is within the dynamic range of the second ADC;

selecting and outputting the first digital signal with the output selector according to the sensed analog signal provided to the output selector if the sensed analog signal is outside the dynamic range of the second ADC; and wherein the output selector receives the first digital output signal for all analog output signals over the entire dynamic range of the first ADC and the output selector receives the second digital output signal for all analog output signals over the entire dynamic range of the second ADC.

17. The method of claim 16, wherein the first digital signal has a first resolution and the second digital signal has a second resolution, wherein the second resolution is greater than the first resolution.

18. The method of claim 16, further comprising performing, with signal processing electronics, linearization, temperature compensation, calibration, and/or translation on the first digital output signal and the second digital output signal; and wherein the first ADC and the second ADC have a common number of bits.

19. The method of claim 16, wherein the step of sensing the fluid flow in the fluid stream with a sensing element includes heating the fluid flow with a heat source and sensing a temperature of the fluid flow with one or more temperature sensors.

20. The method of claim 16, further comprising reconfiguring the second dynamic range.

* * * * *